US005785674A

United States Patent [19]

Mateen

[11] Patent Number: 5,785,674
[45] Date of Patent: Jul. 28, 1998

[54] DEVICE AND METHOD FOR TREATING GLAUCOMA

[76] Inventor: Ahmed Abdul Mateen, 928 E. Juanita Ave., La Verne, Calif. 91750

[21] Appl. No.: 771,446

[22] Filed: Dec. 20, 1996

Related U.S. Application Data

[63] Continuation-in-part of Ser. No. 269,839, Jul. 1, 1994, Pat. No. 5,616,118, which is a continuation-in-part of Ser. No. 786,734, Oct. 1, 1991, Pat. No. 5,441,473, which is a division of Ser. No. 478,655, Feb. 12, 1990, Pat. No. 5,071,408, which is a continuation-in-part of Ser. No. 255,070, Oct. 7, 1988, abandoned.

[51] Int. Cl.⁶ .................................................... A61M 5/00
[52] U.S. Cl. .................................................... 604/9; 604/8
[58] Field of Search .............................. 604/8, 9, 10, 131, 604/294; 623/4

[56] References Cited

U.S. PATENT DOCUMENTS

| | | | |
|---|---|---|---|
| 3,288,142 | 11/1966 | Hakim | 604/9 |
| 3,910,283 | 10/1975 | LeVeen | 604/9 |
| 4,387,715 | 6/1983 | Hakim et al. | 604/9 |
| 4,521,210 | 6/1985 | Wong | 604/8 |
| 4,560,375 | 12/1985 | Schulte et al. | 604/9 |
| 4,570,901 | 2/1986 | Molteno | 604/8 |
| 4,729,761 | 3/1988 | White | 604/10 X |
| 4,850,955 | 7/1989 | Newkirk | 604/9 |
| 5,454,796 | 10/1995 | Krupin | 604/9 X |
| 5,476,445 | 12/1995 | Baerveldt et al. | 604/9 X |

*Primary Examiner*—Sam Rimell
*Attorney, Agent, or Firm*—John J. Connors; Connors & Assoc.

[57] ABSTRACT

A medical device for treating a patient suffering from glaucoma is adapted to be attached to the globe of the eye of a patient. It includes a distribution plate having a one-way flow valve attached to the anterior end of the plate. The valve is adapted to be placed in communication with fluid to be drained from the intraocular chamber of the eye. There are opposed tab elements that extend outward from each side of the plate at its posterior end. The plate has a predetermined size and shape so that, when attached to the globe of the eye between adjacent rectus muscles with the anterior end from 8 to 10 millimeters from the limbus of the eye, the width of the plate is sufficiently restrictive so that one side is close but not touching one rectus muscle and the other side is close but not touching the other rectus muscle. The length of the plate is sufficiently restrictive so that the posterior end is at least 2 millimeters from the optic nerve of the eye. One tab element is seated beneath one rectus muscle nearby the point where said one rectus muscle is attached to the globe and the other tab element is seated beneath the other rectus muscle nearby the point where said other rectus muscle is attached to the globe.

20 Claims, 2 Drawing Sheets

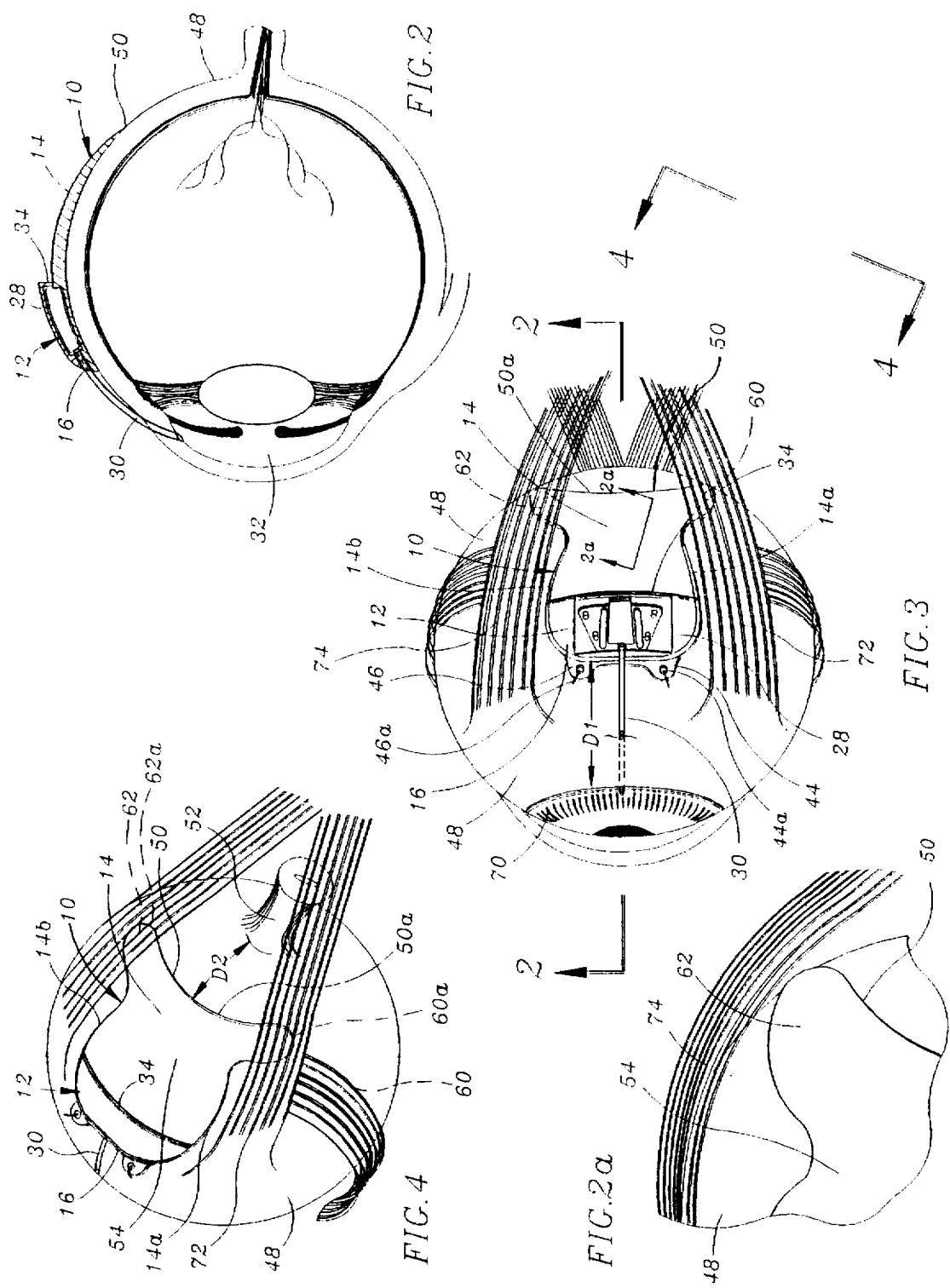

5,785,674

DEVICE AND METHOD FOR TREATING GLAUCOMA

RELATED APPLICATIONS

This application is a continuation-in-part application of U.S. Ser. No. 08/269,839, filed Jul. 1, 1994, entitled "Uniquely Shaped Ophthalmological Device, now U.S. Pat. No. 5,616,118, which is a continuation-in-part application of U.S. Ser. No. 07/786,734, entitled "Medical Valve," filed Oct. 1, 1991, now U.S. Pat. No. 5,441,473, which is a divisional application of U.S. Ser. No. 07/478,655, filed Feb. 12, 1990, and entitled "Medical Valve," now U.S. Pat. No. 5,071,408, which is continuation-in-part application of U.S. patent application Ser. No. 07/255,070, entitled Self-Regulating Pressure Control Glaucoma Valve, filed Oct. 7, 1988 now abandoned. All of these related applications are incorporated herein by reference and made a part of this application.

BACKGROUND OF THE INVENTION

1. Field of the Invention:

This invention relates to a medical device and method for treating a patient suffering from glaucoma.

2. Background Discussion:

As disclosed in U.S. Pat. Nos. 5,071,408, and 5,411,473, glaucoma is treated using a medical valve that employs a membrane in tension to control the flow of excess fluid from the intraocular chamber of the eye. The valve is attached to a distribution plate on which the fluid is deposited upon leaving the valve. This plate may be curved as a segment of a sphere in order to conform to the shape of the globe of the eye. The assembly of valve and distribution plate is placed beneath the layer of tissue forming the surface the globe. This tissue forms a bleb, which is a wall of tissue surrounding the assembly of the valve and distribution plate. The fluid collected on the distribution plate is absorbed by the patient's body through the wall of the bleb. Typically these types of devices are placed between adjacent rectus muscles. If the distribution plate is too large, or not properly shaped, the formation of the bleb may cause the rectus muscles to be pulled inward towards each other. This produces strabismus, that is, the patient's eyes become crossed.

SUMMARY OF THE INVENTION

It is the objective of this invention to provide an assembly of a one-way flow valve and a distribution plate which has a unique configuration that minimizes the likelihood of strebismis.

This invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENT," one will understand how the features of this invention provide its benefits, which include ease of use and minimizing the likelihood of strebismis.

The first feature of medical device of this invention is that it is adapted to be attached to the globe of the eye of a patient. It includes a distribution plate with a one-way flow valve adapted to be placed in communication with fluid to be drained from the intraocular chamber of the eye. The distribution plate has an anterior end, a posterior end, opposed sides extending between said anterior and posterior ends, a curved configuration so that said plate conforms essentially with the spherical shape of the globe of the eye ball, and opposed tab elements that extend outward from each side at said posterior end. The valve is attached to the anterior end of the distribution plate.

The second feature is that the plate has a predetermined size and shape to maximize the area of the bleb, yet prevent strebismis. The larger the area of the bleb, the more rapidly the fluid will be absorbed by the patient's body, which is desirable to avoid high within the bleb. When attached to the globe between adjacent rectus muscles with the anterior end from 8 to 10 millimeters (mm) from the limbus of the eye, the width of the plate is sufficiently restrictive so that one side is close but not touching one rectus muscle and the other side is close but not touching the other rectus muscle, and the length of the plate is sufficiently restrictive so that the posterior end is at least 2 millimeters from the optic nerve of the eye. With the plate in this precise location on the globe, one tab element is seated beneath one rectus muscle nearby the point where said one rectus muscle is attached to the globe and the other tab element is seated beneath the other rectus muscle nearby the point where said other rectus muscle is attached to the globe.

Specifically, the distribution plate has the following characteristics. Each side of the plate is less than 0.5 millimeter from an adjacent rectus muscles. The total area of the plate, inclusive of the surface area carrying the valve, is from 240 to 260 square millimeter. The valve occupies less than 30 percent of the surface area of the distribution plate. The sides of the plate slope inward towards each other to a narrow section having a breath of from 13 to 14 millimeters, and then slope outward to form the tab elements. The anterior end has a width from 13 to 15 millimeters, and the posterior end of the plate curves inward between the tab elements. The tab elements each have a surface area of from 20 to 30 square millimeters, and they have rounded tips separated by a distance of from 16 to 18 millimeters.

The third feature is that one-way flow valve includes a body member holding a pair of overlying elastic membranes in tension to form therebetween a pressure chamber. The membranes provide an elongated, slit-like opening therebetween, which is normally in a closed position and opens when the pressure in the pressure chamber exceeds a predetermined pressure and returns to the closed position when the pressure in the pressure chamber is below the predetermined pressure. An inlet tube in communication with and connected to the pressure chamber at a point remote from the opening places the valve in communication with the intraocular chamber of the eye.

This invention also includes a method for treating glaucoma by draining fluid from the intraocular chamber of a patient's eye. This method includes the following steps:

(a) providing a medical device including a distribution plate having an anterior end, a posterior end, opposed sides extending between said anterior and posterior ends, a curved configuration conforming essentially to the spherical shape of the globe of the eye ball, and opposed tab elements that extend outward from each side at said posterior end, and a one-way flow valve attached to the anterior end of the distribution plate having a tube adapted to be placed in communication with the fluid to be drained from the intraocular chamber of the eye, (b) positioning the device on the globe between adjacent rectus muscles with the anterior end from 8 to 10 millimeters from the limbus of the eye, with the width of the plate being sufficiently restrictive so that one side is close but not touching one rectus muscle and the other side is close but not touching the other rectus muscle, and the length of the plate being sufficiently restrictive so that the posterior end is at least 2 millimeters inch from the optic nerve of the eye, (c) inserting one tab element beneath one rectus muscle nearby the point where said one rectus muscle is attached to the globe and inserting the other tab element beneath the other rectus muscle nearby the point where said other rectus muscle is attached to the globe, (d) placing the tube in communication with the intraocular chamber of the eye so that the fluid drains from the intraocular chamber onto the distribution plate under the control of the valve, and (e) attaching said device to the globe.

DESCRIPTION OF THE DRAWING

The preferred embodiment of this invention, illustrating all its features, will now be discussed in detail. This embodiment depicts the novel and non-obvious medical device and method of this invention as shown in the accompanying drawing, which is for illustrative purposes only. This drawing includes the following figures (FIGS.), with like numerals indicating like parts:

FIG. 2 is a cross-sectional view taken along line 2—2 of FIG. 3.

FIG. 3 is a side view of the globe of an eye having the medical device of this invention attached to the globe.

FIG. 4 is a perspective view taken along line 4—4 of FIG. 3.

FIG. 2a is an enlarged, fragmentary view taken along line 2a—2a of FIG. 3.

DESCRIPTION OF THE PREFERRED EMBODIMENT

Figure 1:
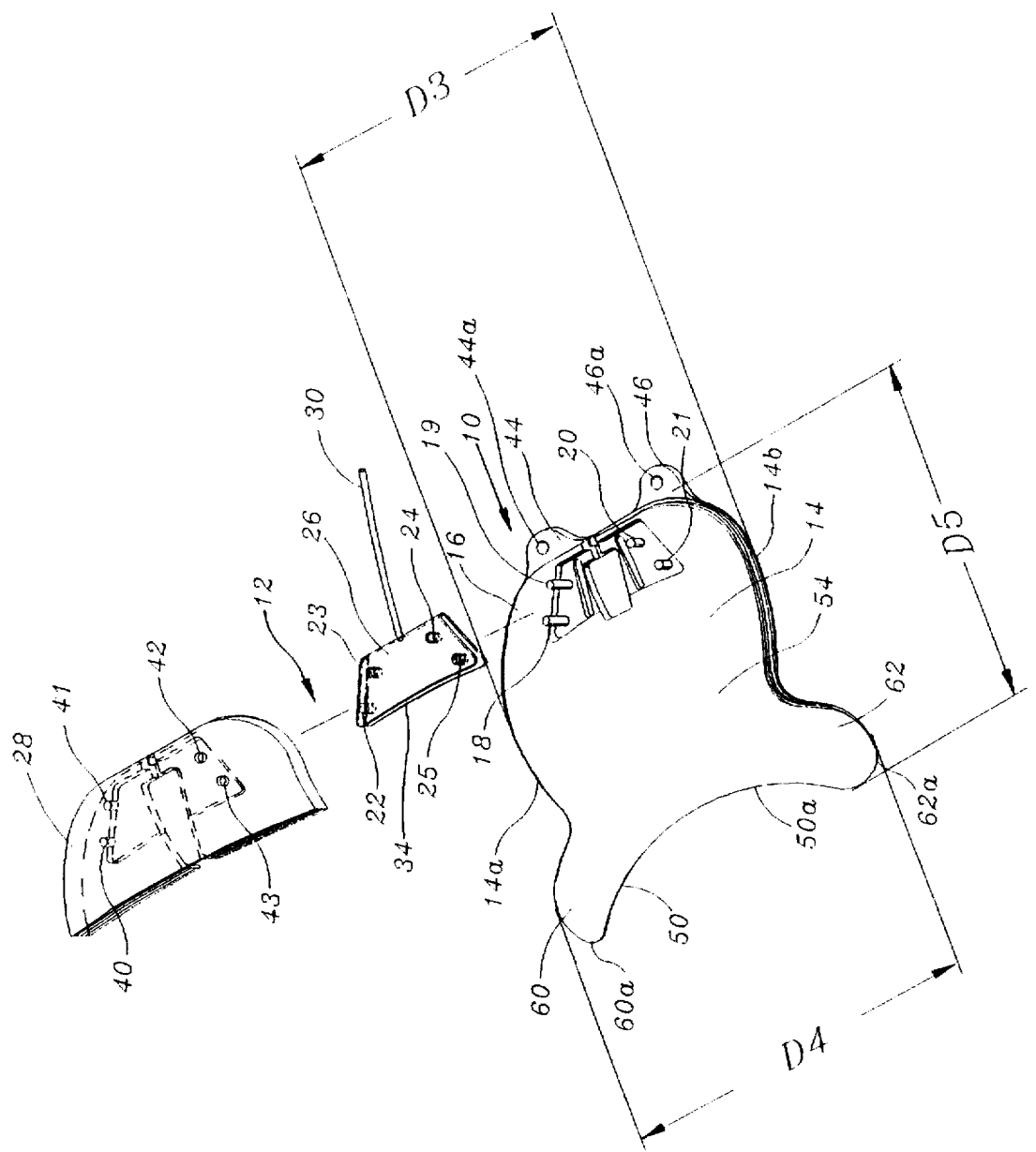
FIG. 1 is an exploded view of the medical device of this invention.

As best shown in FIG. 1, the medical device 10 of this invention includes an assembly of a one-way flow valve 12 and a distribution plate 14. The distribution plate 14 has a unique shape, with the valve 12 attached to the anterior end 16 of the plate. The anterior end 16 of the plate 14 has four posts 18 through 21 which fit through aligned holes 22 through 25 in a folded membrane 26, with a cover 28 covering the membrane, which is mounted on the plate 14. The folded membrane 26 is sandwiched between the plate 14 and the cover 28, with the posts 18 through 21 extending into aligned holes 40 through 43 in the cover 28. This valve 12 includes a tube 30 made of a flexible material, which has one end attached to the folded membrane 26 and another end adapted to be inserted into the intraocular chamber 32 of the eye, as illustrated in FIG. 2. Opposite the end where the tube 30 is attached, the membrane 26 forms a slit-like opening 34. With the cover 28 in place, the membrane 26 is in tension, and the slit-like opening 34 is normally closed until the pressure inside the intraocular chamber 32 exceeds a predetermined level. When this predetermined pressure is reached, the slit-like opening 34 expands to release fluid, which flows onto the distribution plate 14. This valve 12 is disclosed in detail in U.S. Pat. Nos. 5,071,408 and 5,411,473.

At the anterior end 16 are a pair of spaced apart fingers 44 and 46 which have orifices 44a and 46a in them. These orifices 44a and 46a are used to hold sutures which are threaded through the orifices to attach the medical device 10 to the globe 48 of the patient's eye. After cutting a flap (not shown) of upper layer tissue in the globe 48, the medical device 10 is placed under this flap and the sutures are threaded through the orifices 44a and 46a and more sutures are used to sew the flap in place after it is positioned to cover the medical device. The medical device 10 is now located on the globe in the correct position shown in FIGS. 2 through 4 with the flap (not shown) covering the device.

A characteristic of this invention is the size and shape of the distribution plate 14, which has been designed to maximize the surface area of the distribution plate 14 without causing strebismis. In accordance with this invention, the anterior end 16 of the plate 14 is a distance of 8 millimeters (D1) from the limbus 70 (FIG. 3) of the patient's eye. The posterior end 50 of the distribution plate 14 has an inwardly curved edge 50a. This inwardly curved edge is desirable to ensure that, when the device 10 is properly placed in the correct position on the globe 48 of the patient's eye, this end 50 is at least 2 millimeters (D2) away from the optic nerve 52 (FIG. 4). This distance may range between 2 and 4 millimeters. The anterior end 16 of the distribution plate 14 has a width (D3), as measured from the greatest separation of the sides 14a and 14b, of from 13 to 15 millimeters. The sides 14a and 14b of the plate 14 curve outward slightly, and then inward to form a narrow section 54. The sides 14a and 14b then expand outward to form at the posterior end 50 on the opposite sides 14a and 14b the tabs 60 and 62, respectively. The tips 60a and 62a of these tabs 60 and 62 are rounded slightly and are separated a distance (D4) ranging between 16 and 18 millimeters. The area of these tabs is typically about 25 square millimeters. The total length (D5), not including the fingers 44 and 46, of the distribution plate 14 ranges between 14 and 16 millimeters. The total area of the distribution plate 14 is 250 square millimeters, inclusive of the area occupied by the valve 12. Typically the valve 12 does not occupy more than 30 percent of the surface of the plate 14.

As depicted in FIG. 2a, the unique shape of the distribution plate 14 allows it to be seated between adjacent pairs of rectus muscles 72 and 74, with each tab 60 and 62, respectively, positioned beneath the rectus muscles 72 and 74 near the point where each rectus muscle joins the globe 48. The plate 14 fills almost completely the space between the rectus muscles when it is correctly located on the globe 48, as depicted in FIG. 3. The bleb (not shown) formed over this medical device 10 does not overlap the rectus muscles, or otherwise interfere with them, thus minimizing the likelihood of strebismis.

The device 10 is relatively simple to implant. As disclosed in U.S. Pat. No. 5071408, a special instrument may be used to insert the tube 30 into the intraocular chamber 32 of the eye so that the one end of the tube is in communication with the fluid in the chamber. When the pressure in the chamber 32 is too great, excess fluid flows through the tube 30 into the valve 12, causing the membrane 26 to expand, opening the slit 34 so the fluid flows onto the plate 14.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention:

I claim:

1. A medical device for treating a patient suffering from glaucoma and adapted to be attached to the globe of the eye of a patient, including a distribution plate having an anterior end, a posterior end, opposed sides extending between said anterior and posterior ends, a curved configuration so that said plate conforms essentially with the spherical shape of the globe of the eye ball, and opposed tab elements that extend outward from each side at said posterior end, said plate upon being attached to the globe one tab element being seated beneath one rectus muscle nearby the point where said one rectus muscle is attached to the globe and the other tab element being seated beneath the other rectus muscle nearby the point where said other rectus muscle is attached to the globe, and a one-way flow valve attached to the anterior end of the distribution plate adapted to be placed in communication with fluid to be drained from the intraocular chamber of the eye.

2. The medical device of claim 1 where each side of the plate is less than 0.5 millimeter from an adjacent rectus muscles.

3. The medical device of claim 1 where the total area of the distribution plate inclusive of the surface area carrying the valve is from 240 to 260 square millimeters.

4. The medical device of claim 3 where the valve occupies less than 30 percent of the surface area of the distribution plate.

5. The medical device of claim 1 where the sides slope inward towards each other to a narrow section having a width of from 13 to 15 millimeters, and then slope outward to form said tab elements.

6. The medical device of claim 1 where the anterior end has a width from 13 to 15 millimeters.

7. The medical device of claim 1 where the posterior end of the plate curves inward between said tab elements.

8. The medical device of claim 1 where the tab elements each have a surface area of from 20 to 30 square millimeters.

9. The medical device of claim 1 where the tab elements have rounded tips, said tips being separated by a distance of from 16 to 18 millimeters.

10. The medical device of claim 1 where the one-way flow valve includes a body member holding a pair of overlying elastic membranes in tension to form therebetween an pressure chamber, said membranes providing an elongated, slit-like opening therebetween, which is normally in a closed position and opens when the pressure in the pressure chamber exceeds a predetermined pressure and returns to the closed position when the pressure in the pressure chamber is below said predetermined pressure, and an inlet tube in communication with and connected to the pressure chamber at a point remote from the opening.

11. A medical device for treating a patient suffering from glaucoma and adapted to be attached to the globe of the eye of a patient, including a distribution plate having an anterior end, a posterior end, opposed sides extending between said anterior and posterior ends, a curved configuration so that said plate conforms essentially with the spherical shape of the globe of the eye ball, and opposed tab elements that extend outward from each side at said posterior end, sides sloping inward towards each other to a narrow section having a width of from 13 to 15 millimeters, and then slope outward to form said tab elements, said plate having total area of from 240 to 260 square millimeters and upon being attached to the globe one tab element being seated beneath one rectus muscle nearby the point where said one rectus muscle is attached to the globe and the other tab element being seated beneath the other rectus muscle nearby the point where said other rectus muscle is attached to the globe, and a one-way flow valve attached to the anterior end of the distribution plate adapted to be placed in communication with fluid to be drained from the intraocular chamber of the eye, said one-way flow valve including a body member holding a pair of overlying elastic membranes in tension to form therebetween an pressure chamber, said membranes providing an elongated, slit-like opening therebetween, which is normally in a closed position and opens when the pressure in the pressure chamber exceeds a predetermined pressure and returns to the closed position when the pressure in the pressure chamber is below said predetermined pressure, and an inlet tube in communication with and connected to the pressure chamber at a point remote from the opening.

12. The medical device of claim 11 where the valve occupies less than 30 percent of the total surface area of the distribution plate.

13. The medical device of claim 11 where the anterior end has a width from 13 to 15 millimeters.

14. The medical device of claim 11 where the posterior end of the plate curves inward between said tab elements.

15. The medical device of claim 11 where the tab elements each have a surface area of from 20 to 30 square millimeters.

16. The medical device of claim 11 where the tab elements have rounded tips, said tips being separated by a distance of from 16 to 18 millimeters.

17. A method for treating glaucoma by draining fluid from the intraocular chamber of a patient's eye, including the steps of (a) providing a medical device including a distribution plate having an anterior end, a posterior end, opposed sides extending between said anterior and posterior ends, a curved configuration conforming essentially to the spherical shape of the globe of the eye ball, and opposed tab elements that extend outward from each side at said posterior end, and a one-way flow valve attached to the anterior end of the distribution plate having a tube adapted to be placed in communication with the fluid to be drained from the intraocular chamber of the eye, (b) positioning the device on the globe between adjacent rectus muscles with the anterior end from 8 to 10 millimeters from the limbus of the eye, with the width of the plate being sufficiently restrictive so that one side is close but not touching one rectus muscle and the other side is close but not touching the other rectus muscle, and the length of the plate being sufficiently restrictive so that the posterior end is at least 2 millimeters from the optic nerve of the eye, (c) inserting one tab element beneath one rectus muscle nearby the point where said one rectus muscle is attached to the globe and inserting the other tab element beneath the other rectus muscle nearby the point where said other rectus muscle is attached to the globe, (d) placing the tube in communication with the intraocular chamber of the eye so that the fluid drains from the intraocular chamber onto the distribution plate under the control of the valve, and (e) attaching said device to the globe.

18. The method of claim 17 where the total area of the distribution plate inclusive of the surface area carrying the valve is from 240 to 260 square millimeters.

19. The method of claim 18 where the valve occupies less than 30 percent of the total surface area of the distribution plate.

20. The method of claim 19 where the one-way flow valve includes a body member holding a pair of overlying elastic membranes in tension to form therebetween an pressure chamber, said membranes providing an elongated, slit-like opening therebetween, which is normally in a closed position and opens when the pressure in the pressure chamber exceeds a predetermined pressure and returns to the closed position when the pressure in the pressure chamber is below said predetermined pressure, and an inlet tube in communication with and connected to the pressure chamber at a point remote from the opening.

* * * * *

UNITED STATES PATENT AND TRADEMARK OFFICE
CERTIFICATE OF CORRECTION

PATENT NO. : 5,785,674
DATED : July 28, 1998
INVENTOR(S) : AHMED, A. Mateen

It is certified that error appears in the above-identified patent and that said Letters Patent is hereby corrected as shown below:

Delete the word "inch" in column 3, line 6
Delete the word "muscles" in column 5, line 30 and substitute in place thereof --muscle--
Delete the word "an" in column 5, line 53 and substitute in place thereof --a--
Delete the word "an" in column 6, line 22 and substitute in place thereof --a--

Signed and Sealed this

Fourth Day of January, 2000

Attest:

*Attesting Officer*      *Acting Commissioner of Patents and Trademarks*

UNITED STATES PATENT AND TRADEMARK OFFICE
CERTIFICATE OF CORRECTION

PATENT NO. : 5,785,674
DATED : Jul. 28, 1998
INVENTOR(S) : Abdul Mateen Ahmed

It is certified that error appears in the above-identified patent and that said Letters Patent is hereby corrected as shown below:

On the title page, item [76],
Delete the name of the inventor "Ahmed Abdul Mateen" and substitute in place thereof --A. Mateen Ahmed--

Item [19] should read --Ahmed--

Signed and Sealed this

Sixth Day of June, 2000

Attest:

Q. TODD DICKINSON

*Attesting Officer*  *Director of Patents and Trademarks*